United States Patent [19]

Bacon

[11] Patent Number: 5,447,150

[45] Date of Patent: Sep. 5, 1995

[54] MEDICAMENT DISPENSING DEVICE

[75] Inventor: Raymond Bacon, Portsmouth, England

[73] Assignee: Norton Healthcare Limited, Essex, Great Britain

[21] Appl. No.: 39,302

[22] PCT Filed: Nov. 29, 1991

[86] PCT No.: PCT/GB91/02118

§ 371 Date: Apr. 22, 1993

§ 102(e) Date: Apr. 22, 1993

[87] PCT Pub. No.: WO92/09323

PCT Pub. Date: Jun. 11, 1992

[30] Foreign Application Priority Data

Dec. 1, 1990 [GB] United Kingdom ............... 9026191

[51] Int. Cl.6 .................................... A61M 11/00
[52] U.S. Cl. ......................... 128/200.14; 128/200.23
[58] Field of Search ...................... 128/200.14, 200.23, 128/204.23, 204.26, 202.22

[56] References Cited

U.S. PATENT DOCUMENTS

| | | | |
|---|---|---|---|
| 3,187,748 | 6/1965 | Mitchell et al. | 128/200.23 |
| 3,598,294 | 8/1971 | Hedrick et al. | 128/200.23 |
| 3,605,738 | 9/1971 | Ciranna | 128/200.23 |
| 3,789,843 | 2/1974 | Armstrong et al. | 128/200.23 |
| 4,484,577 | 11/1984 | Sackner et al. | 128/200.23 |
| 4,796,614 | 1/1989 | Nowacki et al. | 128/200.23 |
| 5,069,204 | 12/1991 | Smith et al. | 128/200.23 |
| 5,184,761 | 2/1993 | Lee | 128/200.23 |
| 5,217,004 | 6/1993 | Blasnik et al. | 128/200 |

*Primary Examiner*—Edgar S. Burr
*Assistant Examiner*—Aaron J. Lewis
*Attorney, Agent, or Firm*—Nikaido Marmelstein Murray & Oram

[57] ABSTRACT

A metered dose inhaler for use with a pressurised aerosol container which is preferably breath-actuated. A preload (80) is applied to the internal aerosol valve by an amount sufficient to result in a dose release, but this is prevented by the application of a pneumatic resisting force (130). The inhaler comprises a release device (110) which, upon actuation, releases the resisting force and allows the preload to actuate the aerosol valve (135). A metered dose of medicament is then released for inhalation by the patient.

24 Claims, 5 Drawing Sheets

FIG. 5.
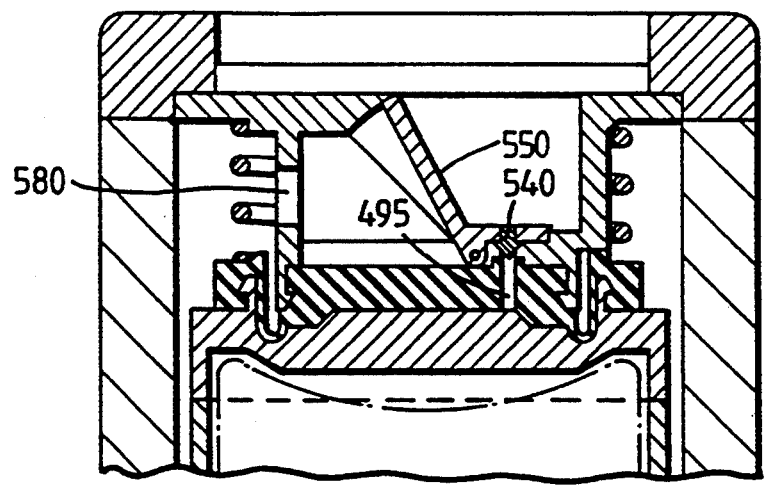
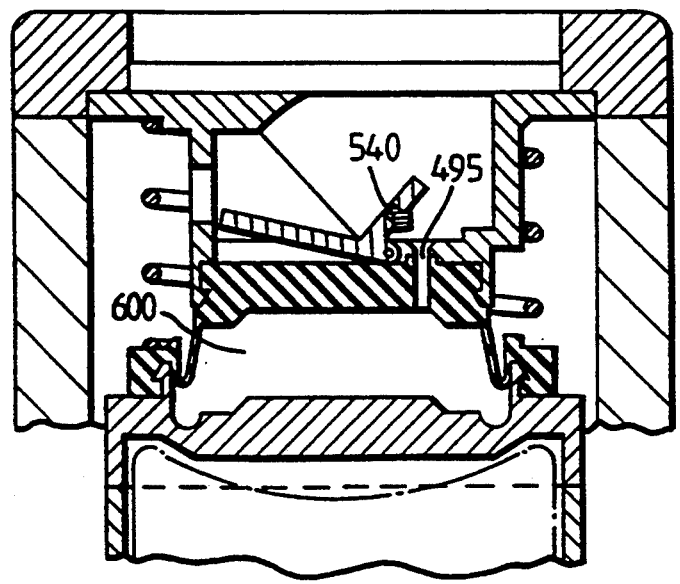

MEDICAMENT DISPENSING DEVICE

This invention relates to a dispensing device, and more specifically, to a device suitable for dispensing discrete amounts of fluid.

In particular, the invention is concerned with a dispensing device of the type where the metered dose is administered in response to the inhalation of the patient.

Metered dose inhalers are well known in medicine for treatment, or alleviation of the effects of respiratory complaints, for example asthma. Breath-actuated devices are also known, and have been the subject of many patent applications.

GB 1288971; GB 1297993; GB 1335378; GB 1383761; GB 1392192; GB 1413285; W085/01880; GB 2204799; U.S. Pat. No. 4,803,978 and EP 0186280A describe inhalation-actuated dispensing devices for use with a pressurised aerosol dispensing container. The device includes a dispensing container and the container includes a valve capable of releasing a metered amount of the aerosol contents, when an internal spring operating the valve is compressed by a sufficient amount. The dispensing device often comprises a chamber having a mouthpiece, air inlets, actuating means for causing the actuation of the valve in the dispensing container, a latching means for releasably retaining said metering valve in a charged position, and an inhalation responsive means for releasing the latch, such that a metered amount of aerosol compound is discharged into the region of the mouthpiece. The overall objective is to give co-ordination of discharge of medicament from the aerosol container with inhalation of the patient, thus allowing a maximum dose of medicament to reach the bronchial passages of the lungs.

The latching means is often connected to a valve which moves from a latching position to a dispensing position in response to a partial vacuum developed upon inhalation.

EP-A-0045419 describes an inhalation device having biassing means which are alone of insufficient force to depress the container but which together are of sufficient force to do so.

EP-A-186280 describes a device which employs magnets to control the release of the aerosol container.

U.S. Pat. No. 3,605,738 describes devices in which the aerosol container communicates with the mouthpiece via a metering chamber. A metered quantity of the aerosol compound is discharged into the metering chamber and this is conveyed to the mouthpiece via an inhalation-actuated valve.

GB 1269554 describes a device wherein the aerosol container is moveable by a lever and cam system into a charged position held by a latch, a pressure differential acting to trip the latch and move the valve of the container to a discharge position.

It is the object of this invention to provide a metered dose inhaler, wherein the release of the medicament is actuated by the inhalation of the patient. It is a further object of the invention to provide an inhalation-actuated device which is more simple and compact than the prior art dispensers.

According to one aspect of the present invention there is provided a dispensing device for use with a drug delivery system comprising a means for releasing a measured dose of medicament from the system, the releasing means comprising a means for applying a preload capable of actuating the delivery means in the system, a means for applying a resisting pneumatic force capable of preventing actuation of the delivery means and a release device capable of freeing the resisting pneumatic force to allow the preload to actuate the delivery means and dispense the medicament.

The pneumatic resisting means may be provided by air which is either held at a positive pressure greater than atmospheric or a negative pressure below atmospheric prior to release. The release device will act to return the pressure to atmospheric or prior equilibrium, thus allowing the full force of the preload to act.

The device is particularly suited for use with pressurised inhalation aerosols having valves as the delivery means.

Although this device has been described in particular relation to a system using air, it will be realised that in a closed system any suitable gas could be used.

In a preferred arrangement, there is provided a receptacle for an aerosol dispensing container. The receptacle may comprise an outer chamber having a mouthpiece to allow inhalation by a patient using the device. The receptacle may further include one or more air inlets to allow air to pass to the mouthpiece. An inner sleeve enclosing the main body of the aerosol container may be included within the outer chamber. The outer chamber is defined at one end by a cross member which accomodates the valve of the aerosol and seals the chamber apart from providing an aerosol outlet. The inner sleeve is preferably sealed such that there is sliding air tight contact with the outer chamber such that the aerosol container and inner housing provide a piston effect against the cross member to form the resisting load in the form of a high pressure volume capable of preventing the actuation of the aerosol valve.

In a further preferred arrangement, there is provided a receptacle for the aerosol dispensing container. The receptacle may comprise an outer chamber having a mouthpiece to allow inhalation by a patient using the device. The receptacle may further include one or more air inlets to allow air to pass to the mouthpiece. An inner sleeve enclosing the top portion of the main body of the aerosol container may be included within the outer chamber. This inner sleeve is preferably arranged to form one end of an air tight piston cylinder, bellows or diaphragm, such that movement of the inner sleeve will result in an increase in the enclosed volume within the piston cylinder, bellows or diaphragm producing a vacuum or low pressure volume to form the resisting load (force) capable of preventing the actuation of the aerosol valve.

In one embodiment, the sleeve for the dispenser will act as a sliding, air tight piston, except that instead of providing a high pressure volume, downwards motion away from the main casing creates a low pressure volume.

In a favoured arrangement, the pneumatic resisting means may be formed by the inner sleeve and a fixed insert in the outer chamber linked together by flexible bellows or by a sliding air tight seal between the sleeve and a cylinder-like extension to the insert.

In a further embodiment, the preload is a spring which operates against the aerosol valve. Preferably the preload is applied by a lever, pivoted in a recess housed in the outer chamber. The lever may take the form of a restraining lever preventing a loaded spring from acting on the aerosol can until operated. After operation the lever is used to reload the spring. Alternatively the lever may be connected via a plug to a spring which is in contact with the inner sleeve such that movement of the lever loads the spring.

It is also preferred that the release device is breath-actuated in order to co-ordinate the release of the medicament with the intake of breath. The release device may comprise a valve port in the cross member. The valve port may normally be covered by a flexible valve flap which on actuation is opened, allowing the preload to actuate the aerosol valve as pressure in the pneumatic means returns to the rest state. In the embodiment wherein the resisting force is a positive pressure of air, opening of the valve port releases the built-up pressure, and air escapes from the enclosed volume, allowing the full force of the preload to act against the aerosol valve. In the embodiment wherein the resisting force is a vacuum or near vacuum, opening of the valve port allows air to enter the enclosed volume, again allowing the full force of the preload to act against the aerosol valve.

The favoured breath-actuating means comprises a moveable vane mechanism. This vane mechanism may be housed in the lower or upper part of the chamber, depending upon the location of the resisting element. A valve seal is preferably attached to said vane, such that on inhalation the vane moves from its rest position to its actuating position, thus moving the valve seal out of contact with the valve port, causing the opening of the valve. The vane mechanism is preferably dynamically balanced, and may be biased towards its closed position, e.g. by a spring.

The outer chamber may include air inlets allowing passage of air to the mouthpiece of the device. The inlets may take the form of slots or of an air porous membrane. The latter is particularly suitable to help filter dust.

The medicament may be a drug per se or on any form of carrier, e.g. including a powder or a gaseous carrier.

The invention will now be described by way of example only, with reference to the accompanying drawings, in which:

FIG. 5 shows an enlarged section view of the diaphragm in position in pre-actuated and actuated state.

Figure 1:
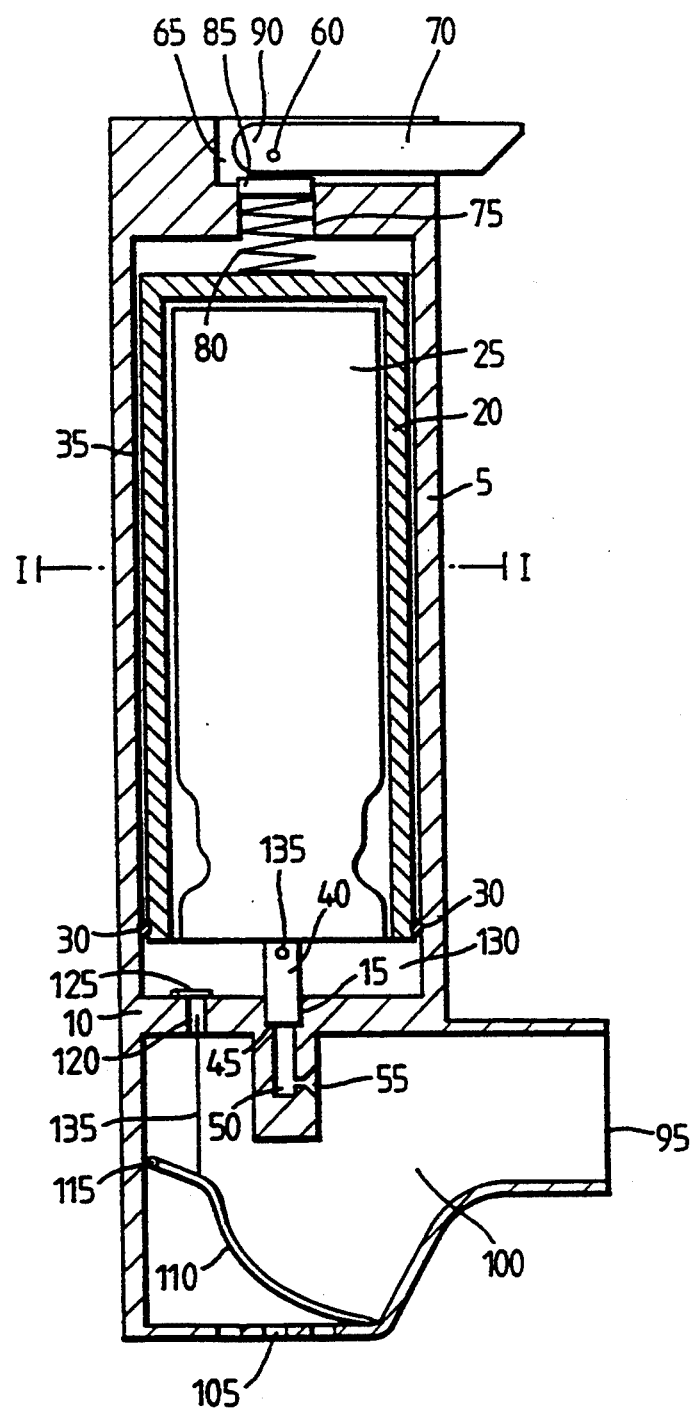
FIG. 1 is a section view of an inhaler, according to a first embodiment of the invention, in the rest position.
Figure 2:
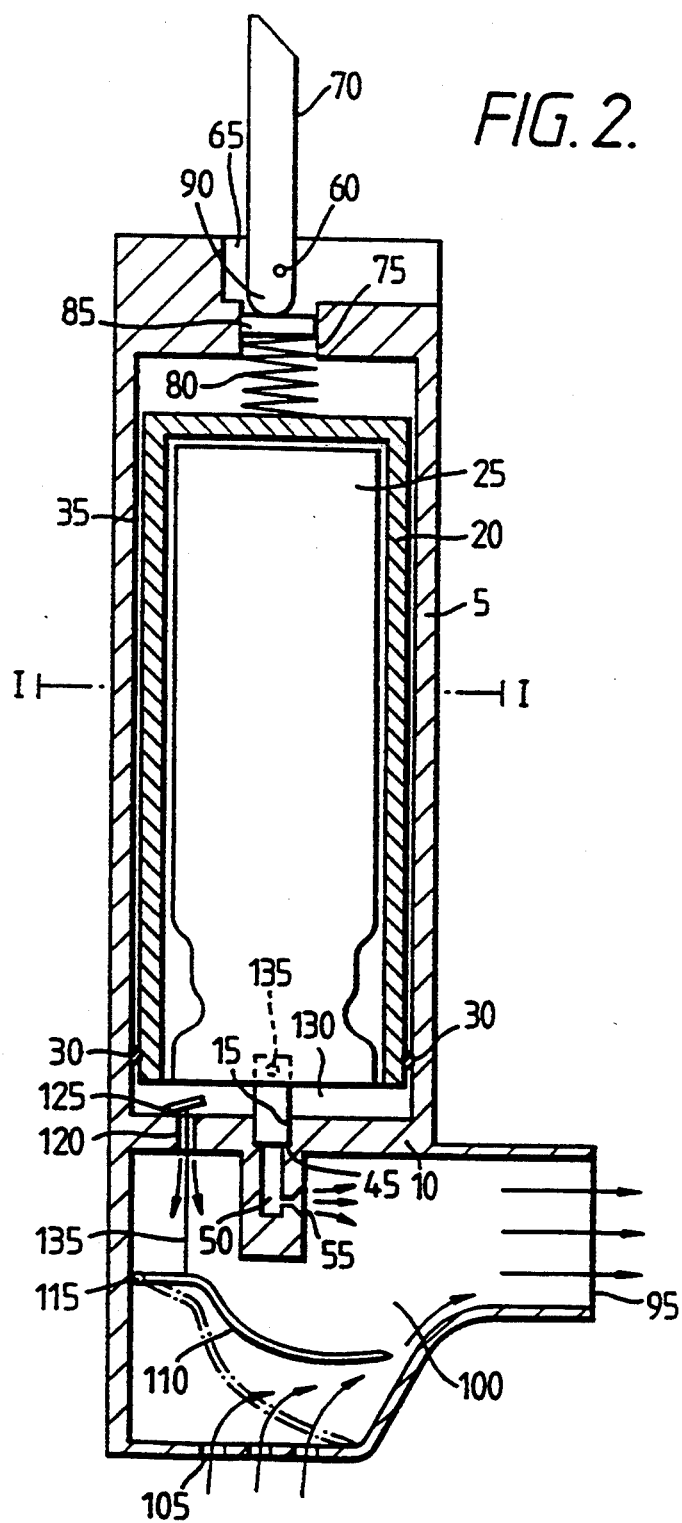
FIG. 2 is a section view of an inhaler according to the first embodiment of the invention during inhalation actuation.

As seen in FIGS. 1 and 2, an inhalation device consists of a main body 5 which is generally cylindrical in cross section. The main body includes a solid cross member 10 having a bore 15 across one end of the main body 5. Within the main body 5 a sleeve 20 is included having a similar cross section to the main body 5. The longitudinal axis of both the sleeve 20 and the main body 5 is generally coaxial. A known type of aerosol dispensing container 25 of generally cylindrical shape is contained within the sleeve 20. The sleeve 20 includes a circumferential seal 30 arranged in sliding air tight contact with the inner bore 35 of the main body 5. The circumferential seal 30 may be a seal of synthetic rubber or natural rubber. The seal may be an 0-ring extending around the sleeve 20. Alternatively the seal 30 could be an integral part of the lip of the sleeve 20.

The aerosol dispensing container 25 has a stem 40 which contains an aerosol dispensing valve [not shown].

The bore 15 is such that it forms an air tight seal on the stem 40 of the aerosol dispensing container 25. A shoulder 45 limits and locates the position of the stem 40, which in turn locates the aerosol dispensing container 25 in position in the main body 5. A passage 50 extends from the bore 15, continuing from the shoulder 45 to interconnect with a dispensing nozzle 55.

As shown in FIG. 1, the end of the main body 5, having a pivot 60 has a recess 65 adapted to receive a cam lever 70 operating on the pivot 60. In the rest position, the pivot extends across the recess 65 allowing the cam lever 70 to rotate about the pivot 60. The recess further includes a generally cylindrical passage 75 which receives a spring 80 located between a slidable plug 85 and the sleeve 20.

As shown in FIG. 2, a cam lever extension 90 when rotated through 90° operates on the plug 85 causing it to slide and compress the spring 80.

At the opposite end of the main body 5 is a mouthpiece 95, separated from the main body by the cross piece 10. The mouthpiece 95 comprises a chamber 100. The dispensing nozzle 55 projects into the chamber 100. The chamber 100 has one or more air inlets 105 such that air may pass from the air inlets 105 to the mouthpiece 95. A vane or flap 110 in its rest position divides the chamber 100 between the air inlets 105 and the mouthpiece 95 [see FIG. 1]. The vane 110 is pivoted by means of a pin 115 such that it may move from its rest position towards the mouthpiece by means of pressure drop between the air inlets 105 [see FIG. 2] and the mouthpiece 95.

The solid cross member 10 includes a small valve port 120 which is covered by a flexible valve flap 125, biased by its construction to rest in a closed position. The flap 125, pivotally connected to the cross piece 10, acts normally to prevent air flow out of the enclosed space 130 and effectively seal the space 130.

A valve stem 135 extends through the valve port 120 and is pivotally connected to the vane 110. On movement of the vane to the actuated position, the stem 135 moves through the valve port 120, causing the flap 125 to be opened. The positioning of the pivoted connection of the valve stem 135 to the vane 110 allows a large movement of the vane to cause a small movement in the valve stem 135, increasing the force applied to the valve flap 125.

In use, the patient loads the aerosol dispensing container into the sleeve 20. The aerosol container may be loaded by providing a coarse threaded screw in the main body 5, positioned above the seal 30, for example about the line I—I. When part of the main body 5 has been unscrewed, the inner sleeve 20 can then be slidably removed and the aerosol inserted. The inner sleeve 20 and main body 5 can then be replaced, and the device is ready for use.

Alternatively, the device could be manufactured as a sealed unit, which is discarded when all the doses in the container have been dispensed.

The lever 70 is in the rest position [see FIG. 1] such that no load is applied via the spring 80 to the sleeve 20. The air space 130 is at atmospheric pressure.

The lever 70 is raised to a loaded position [see FIG. 2] and causes the spring 80 to be compressed by the plug 85, further causing the sleeve 20 and the aerosol container 25 to move downwards. Such movement causes the air in the enclosed space 130 to be compressed. Air cannot escape through the valve port 120 which is covered by the valve flap 125. The increased air pressure in the space 130 acts to provide a resisting load to prevent the actuation of the aerosol valve. It also increases the effectiveness of the sealing of the valve port 120.

Downward movement of the sleeve 20 and container 25 continues until the force being applied by the compressed spring 80 equals the combined force of the internal spring, which actuates the internal valve of the dispensing container, and the force due to the increased pressure in the enclosed space 130. The position of the sleeve 20 and container 25 when the forces balance is determined by the dimensions of the enclosed space and the spring constant of the spring 80; these are chosen such that the balancing of forces occurs just before the aerosol container 25 has been moved, relative to its stem 40, by a sufficient amount to result in a dose release.

Some standard aerosol containers include a stem hole 135 in the stem 40 of the container. In this case, when the cam lever 70 is raised to a loaded position FIG. 2, the air trapped in the enclosed space 130 will vent via the stem hole 140, out through passage 50 and nozzle 55. As the sleeve 20 and container 25 move down further, compressing the internal valve spring, the stem hole 135 is occluded by the valve rubber, and the air in the enclosed space 130 is then compressed.

On inhalation by the patient through the mouthpiece 95, a small pressure differential is created across the vane 110, which is pivoted at one end. The pressure differential causes the vane 110 to move from the rest position to the actuated position. The vane 110 and the design of the lower chamber 100 are such that in the actuated position air can flow freely from the air inlets 105 to the patient.

The upward movement of the vane 110 causes the valve stem 135 to move up into contact with and push open the valve flap 125. Opening the valve flap 125 releases the air compressed in the space 130, thus causing an inbalance of forces on the sleeve 20 and container 25. The sleeve 20 and container 25 are forced downwards by the spring 80 resulting in the release of a measured dose of medicament through the dispensing nozzle 55 and into the mouthpiece 95 at the same time as the patient breathes in. Thus the patient inhales air with a metered dose of medicament.

After the inhalation of the dose by the patient, the cam lever 70 is returned to the rest position. This releases the load on the spring 80, allowing the sleeve 20 and container 25 to move back to their original positions under the influence of the internal valve spring. The volume of the enclosed space 130 is increased, and air flows into the space 130 through the flexible valve flap 125 until the pressure in the space 130 returns to atmospheric pressure.

Figure 3:
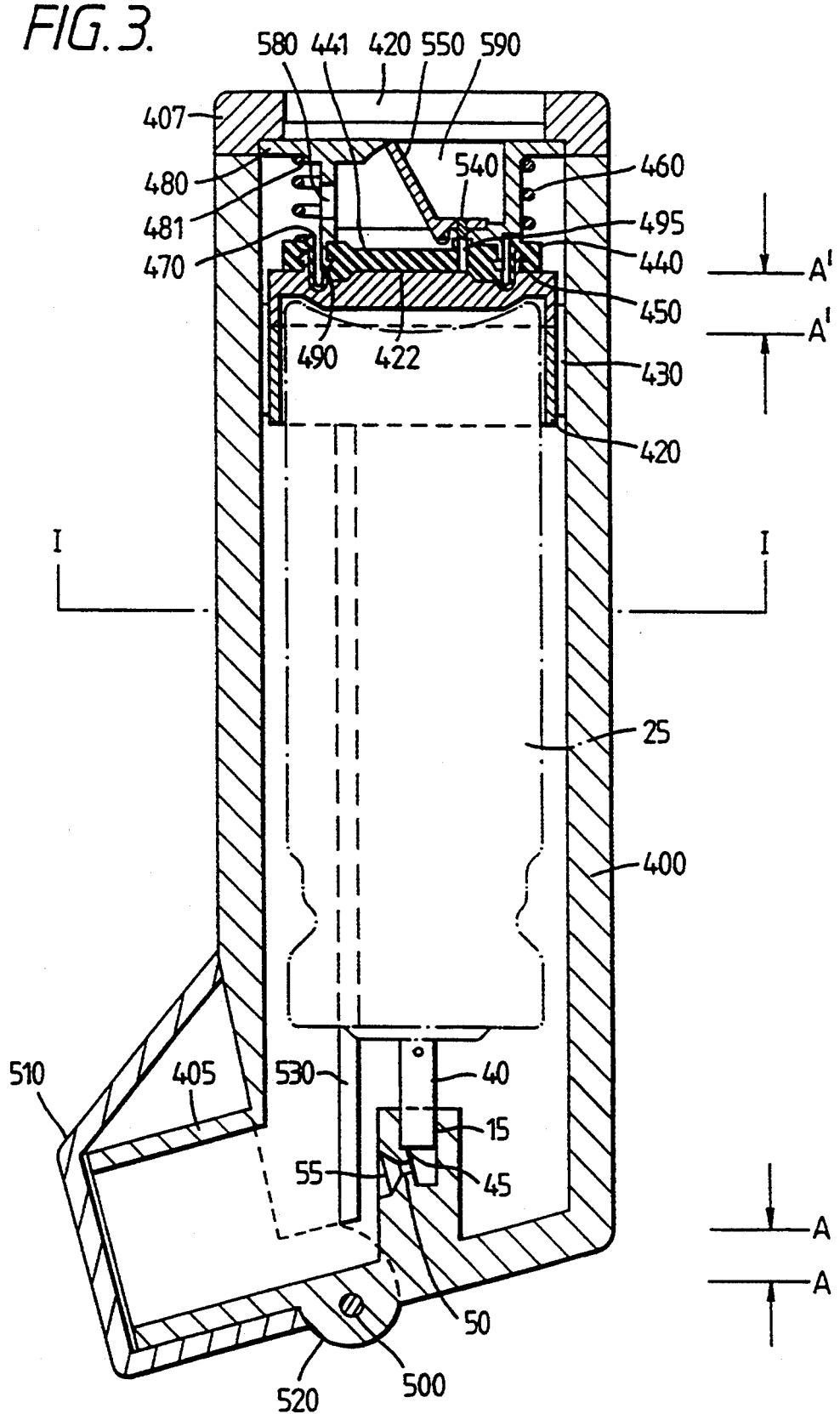
FIG. 3 is a section view of an inhaler according to a second embodiment of the invention.

In an alternative arrangement as shown in FIG. 3, an inhalation device consists of a main body 400 which is generally cylindrical in cross section, with a mouthpiece section 405 at one end and an end cap 407 housing air inlets 420 at the other end. A known type of aerosol dispensing container 25 of generally cylindrical shape is housed within the main body of the device. The aerosol dispensing container has a stem 40 which contains an aerosol dispensing valve (not shown). The bore 15 is such that it forms an air tight seal on the stem 40 of the aerosol dispensing container 25. A shoulder 45 limits and locates the position of the stem 40, which in turn locates the aerosol dispensing container 25 in position in the main body 400. A passage 50 extends from the bore 15, continuing from the shoulder 45 to interconnect with a dispensing nozzle 55.

The opposite end of the dispensing container is contained within a sleeve 420 of similar cross section to the main body 400. The longitudinal axis of both the sleeve 420 and main body 400 is generally coaxial. The sleeve is in loose sliding contact with the inner wall of the main body and may include several rebated grooves 430 in its walls to allow free passage of air in the main body past the sleeve. The sleeve 420 may be held in place by connection with a diaphragm 440 held in connection with the top of the main body 400, as will now be described. Thus, the sleeve 420 effectively hangs from the top of the main body.

Figure 4:
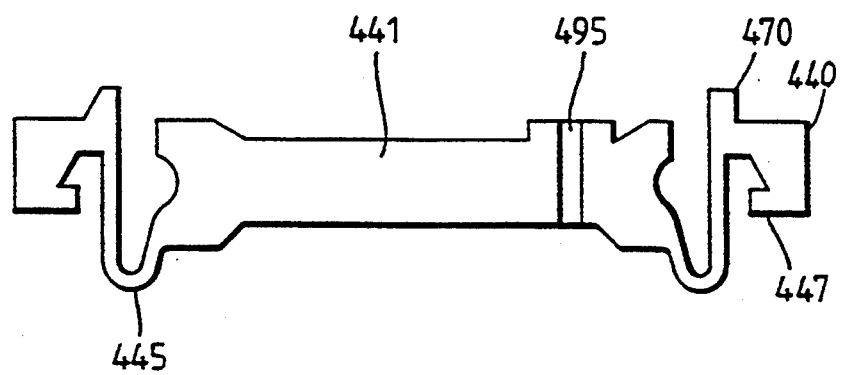
FIG. 4 shows an enlarged view of a diaphragm for use with the embodiment shown in FIG. 3.

One end of an e.g. moulded flexible diaphragm 440 (as shown alone in FIG. 4) comprising a rigid disc-like section 441, a flexible generally cylindrical wall section 445 and a stiffer connector section 447, is fitted around a purpose-made groove 450 in the sleeve, e.g. by snap-fitting. A further moulded lip 470 on the diaphragm provides a snug fit for one end of a compression spring 460. The compression spring is thus located and free to act on the sleeve. The other end of the compression spring is located by an annular shoulder 481 in a predominantly cylindrical flanged insert 480 housed in the top section of the main body 400. This insert includes a groove 490 into which the disc-like section 441 of the flexible diaphragm 440 is snap-fitted.

The joint between the diaphragm connector section 447 and inner sleeve groove 450 is arranged to be air tight and the shape of the top surface of the sleeve 422 to conform to the internal shape of the diaphragm such that in the rest position of the inhaler the two surfaces are in close proximity, and the enclosed space between them very small.

The cylindrical insert 480 is retained in place by the end cap 407 fitted into the main body of the device. This forms a chamber 590 between the air inlet slots 420 and the rigid part 441 of the diaphragm. The chamber is provided with one or more air pathways 580 such that air may pass from the air inlet slots 420 to the mouthpiece 405. The rigid disc-like section 441 of the diaphragm also includes a small valve port 495 which is normally covered by a valve seal (flap) 540 housed in a vane 550 pivotally connected to the insert 480.

The vane 550 in its rest position divides the chamber 590 between the air inlets 420 and the air pathways 580 that link to the mouthpiece such that it may move from its rest position by means of a pressure drop between the air inlets and the mouthpiece. On movement of the vane to the actuated position the valve seal (flap) 540 is sufficiently moved to open the valve port 495. (The vane 550 may be biased closed by a light spring flexure, a weight or a magnet not shown.)

As shown in FIG. 3, the end of the main body having a pivot 500 has a recess adapted to receive a cam 520 integral with a dust cap 510 operating on the pivot. The recess further includes a passage communicating with a similar passage moulded into the internal wall of the main body 400. A camfollower 530 extending from the lower edge of the inner sleeve 420 acts on the cam such that when the dust cap is in the closed position the inner sleeve is forced by the camfollower to its uppermost position.

When the dust cap is rotated to its open position the cam profile is such that the camfollower is free to move downwards by an amount sufficient to allow actuation of the device.

In its rest position the dust cap 510 is closed, the camfollower 530 restrains the inner sleeve 420 in its uppermost position such that the enclosed space trapped between the diaphragm 440 and the top surface 422 of the inner sleeve is at a minimum and the spring 460 is compressed. The valve port 495 is closed by the valve seal (flap) 540 and the sleeve 420 is clear of the top of the aerosol can 25 which is thus unloaded.

The dust cap is opened rotating the integral cam 520 allowing the camfollower 530 to drop by amount AA. The inner sleeve is forced downwards under the action of the spring 460. As the inner sleeve moves downwards the enclosed volume between the diaphragm 440 and inner sleeve is increased by a linear equivalent amount A'A', less than or equal to AA. Since the valve port 495 is closed this creates a low pressure volume or near vacuum in the space 600 [FIG. 5]. The effect of the pressure differential between the enclosed volume 600 and atmospheric pressure is such that the inner sleeve tends to resist the action of the spring. As the inner sleeve moves downwards it contacts the aerosol can 25 and begins compression of the aerosol valve (not shown).

Downward movement of the inner sleeve will continue until there is a balance of forces between the compressive force in the spring 460 and resisting forces created by the pressure differential and compression of the aerosol valve. The geometry of the device is arranged such that this balance occurs before the aerosol valve has been sufficiently compressed to actuate it.

A typical aerosol requires about 20N force to actuate. The spring 460 should accordingly provide a greater force, preferably 10% to 50% greater.

It may also be possible to arrange for the balance of forces to take place before the inner sleeve has contacted the aerosol can, such that the spring force is balanced by the resisting force produced on the inner sleeve by virtue of the pressure differential.

On inhalation by the patient through the mouthpiece 405, a small pressure differential is created across the vane 550 which is pivoted towards one end. The pressure differential causes the vane to move from the rest position to the actuated position. The vane and design of the air passageway 580 in the chamber 590 are such that in the actuated position air can flow freely from the air inlets 420 to the patient.

The movement of the vane 550 causes the valve seal (flap) 540 to be moved out of a sealing position with the valve port 495. Opening the valve port allows air into the gap 600 between the diaphragm and inner sleeve such that the enclosed space reaches atmospheric pressure. This causes an imbalance of forces acting on the sleeve 420 and container 25. The sleeve and container are thus forced downwards by the spring 460 resulting in the release of a measured dose of medicament through the dispensing nozzle 55 and into the mouthpiece at the same time as the patient breathes in. Thus the patient inhales air with a metered dose of medicament.

After the inhalation of the dose by the patient, the dust cap 510 is returned to its closed position. This rotates the cam 520 and causes the camfollower 530 to be forced upwards. This in turn acts on the inner sleeve 420 moving it upwards to compress the spring 460 and close the gap 600 between the diaphragm and inner sleeve top surface 422. This forces air out of the enclosed space 600 which escapes through the valve port 495 lifting the valve seal (flap) 540. Since the valve seal (flap) is only lightly biased to its closed position it presents little resistance to air flow out of the enclosed space. The aerosol can is free to return to the rest position under the action of its own aerosol valve spring.

In use the patient loads the aerosol dispensing container into the main body. The aerosol container may be loaded by providing a coarse threaded screw in the main body 400, for example about the line I—I. When part of the main body 400 has been unscrewed, the aerosol can be inserted. The main body 400 can then be replaced locating the inner sleeve over the top end of the can, and the device is ready for use. As described previously, the device could be manufactured as a sealed unit.

The device may be provided with means to provide a regulated air flow to the user or inhaler. Thus a sonic device, e.g. a reed, may be provided which sounds when the inspired air flow is greater than a pre-set level, e.g. above 30 to 50 litres per minute. The sonic device may be located in the mouthpiece 95 or below the air inlet 420. The sound produced warns the patient to breathe at a lower rate.

The device may also be provided with a means such that it will not operate below a certain pre-determined air flow rate, e.g. 10 to 30 litres per minute. In one embodiment the vane 550 or 110 will be biased by a spring such that the predetermined minimum air flow is necessary for it to move to its actuated position and enable the valve seal to open.

The main body of a dispensing device, as described in the first or second embodiment of this invention is preferably manufactured from a plastic such as polypropylene, acetal or moulded polystyrene. It may however be manufactured from metal or another suitable material.

I claim:

1. A dispensing device for dispensing a medicant in metered doses in a drug delivery system comprising:
   a dispensing device body;
   a sleeve disposed in said body and capable of receiving a medicant dispenser;
   a means for releasing measured dose of medicant comprising a means for applying a preload force to said sleeve, a means for applying a resisting pneumatic force to said sleeve, and a release device capable of freeing the resisting pneumatic force.

2. A device according to claim 1 wherein the drug delivery system comprises a pressurised inhalation aerosol dispensing container having a valve as a delivery means.

3. An inhalation actuable dispensing device for use with a pressurised aerosol dispensing container comprising an inner sleeve capable of receiving a dispensing container, a means for applying a preload force to said sleeve capable of actuating an internal valve of an aerosol container to release a metered dose from a container, a means for applying a resisting pneumatic force to the sleeve capable of preventing actuation of an aerosol valve and an inhalation actuated release device capable of releasing the resisting pneumatic force to allow the preload to actuate an internal valve and allow a metered dose to be dispensed.

4. A dispensing device according to claim 1 or claim 3, further including a receptacle capable of receiving a dispensing container comprising an outer chamber having a mouthpiece and wherein the inner sleeve is included within the outer chamber, the inner sleeve is capable of at least partly enclosing a main body of an aerosol container.

5. A dispensing device according to claim 4 wherein the outer chamber includes one or more inlets to allow air to flow into the mouthpiece.

6. A dispensing device according to claim 3 wherein the inhalation actuated release device is attached to a movable vane, which on inhalation is capable of moving from a rest position to an actuating position.

7. A dispensing device according to claim 6 wherein the vane is biased such that it will move to its actuating position at a predetermined air flow rate, but will not move to said actuating position at a rate therebelow.

8. A dispensing device according to claim 6 wherein the moveable vane is capable of actuating the release device to allow the preload to actuate an aerosol valve.

9. A dispensing device according to claim 3 wherein the means for applying preload is applied by use of a spring which is capable of operating against an aerosol valve.

10. A dispensing device according to claim 3 wherein the pneumatic resisting force comprises a volume of air held at a positive pressure greater than atmospheric.

11. A dispensing device according to claim 10 wherein the preload comprises a lever pivoted in a recess in the dispensing device, the lever being connected via a plug to a spring, the spring being capable of acting on an aerosol container.

12. A dispensing device according to claim 10 wherein the positive pressure is created by cooperation of an aerosol container, the inner sleeve and a cross member to form a piston.

13. A dispensing device according to claim 3 wherein the pneumatic resisting force comprises a volume of air held at a negative pressure below atmospheric.

14. A dispensing device according to claim 13 wherein the negative pressure is created inside an expandable air-tight volume selected from a bellows, piston, cylinder or a diaphragm that is connected to the sleeve.

15. A dispensing device according to claim 13 wherein the preload comprises a spring acting on the inner sleeve and said spring being compressed by a lever acting on the inner sleeve.

16. A dispensing device according to claim 15 wherein said lever urges against a cam formed upon a rotable cover, such that opening of said cover causes the lever to drop and to release energy stored in the spring to act upon the inner sleeve which is capable of acting upon an aerosol container.

17. A dispensing device according to claim 3 which further comprises a sonic device which will sound a signal when a volume of air passing across the sonic device provides the inhaler with an inspiration rate greater than a pre-set rate.

18. A dispensing device according to claim 3 wherein the release device comprises a valve port, normally covered by a valve flap, which is capable of being opened on actuation of the device.

19. A dispensing device for use with a drug delivery system comprising an inner sleeve capable of receiving a dispensing container, a releasing means for releasing a measured dose, preload means for applying a preload force to the sleeve and capable of actuating the releasing means, resisting means for applying a resisting pneumatic force to the sleeve capable of preventing actuation of the releasing means by the preload means, and preload release means for freeing the resisting pneumatic force to allow the preload to actuate the releasing means.

20. A dispensing device for use with a drug delivery system comprising:
a drug delivery system comprising a dispensing container capable of dispensing a metered dose;
a means for releasing a metered dose;
a sleeve capable of receiving said dispensing container;
wherein said releasing means comprises a means for applying a preload force to said sleeve and capable of actuating said container in said system, a means for applying a resisting pneumatic force to said sleeve capable of preventing actuation of said container, and a release device capable of freeing said resisting pneumatic force to actuate said delivery system and dispense said metered dose.

21. A dispensing device for use with an aerosol medicant container for dispensing a medicant in metered doses comprising:
a main body with a first and second end;
a sleeve comprising sides and a base;
a diaphragm comprising a valve port operationally connected to said second end of said main body and said base of said sleeve;
a spring operationally positioned in said second end of said main body so as to apply a preload force to said sleeve; and
a vane operationally attached to said diaphragm wherein said vane has first and second positions, wherein when said vane is in said first position said vane seals said valve port and when said vane is in said second position said valve port is unsealed.

22. A dispensing device as claimed in claim 21, further comprising:
air inlets disposed in said second end of said main body.

23. A dispensing device as claimed in claim 21, further comprising:
a mouthpiece integrally formed in said first end of said main body.

24. A dispensing device as claimed in claim 23, further comprising:
a dust cap pivotally attached to said first end of said main body capable of covering said mouthpiece wherein said dust cap comprises a cam; and
a cam follower disposed in said main body and operationally connected between said cam and said sleeve.

* * * * *

UNITED STATES PATENT AND TRADEMARK OFFICE
Certificate

Patent No. 5,447,150　　　　　　　　　　　　　　　　　　Patented: September 5, 1995

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Raymond Bacon, Portsmouth, England; and Michael John Holroyd, Portsmouth, England.

Signed and Sealed this Twenty-Fifth Day of September 2001.

JOHN G. WEISS
*Supervisory Patent Examiner*
Art Unit 3761